(12) United States Patent
Torgerson et al.

(10) Patent No.: US 6,869,800 B2
(45) Date of Patent: Mar. 22, 2005

(54) MONITORING INSTRUMENT

(75) Inventors: Robert D Torgerson, Houston, TX (US); Peter E J Abbott, Eaglescliffe (GB)

(73) Assignee: Imperial Chemical Industries PLC, London (GB)

( * ) Notice: Subject to any disclaimer, the term of this patent is extended or adjusted under 35 U.S.C. 154(b) by 185 days.

(21) Appl. No.: 10/041,553

(22) Filed: Jan. 10, 2002

(65) Prior Publication Data

US 2002/0059842 A1 May 23, 2002

Related U.S. Application Data

(63) Continuation of application No. PCT/GB00/02519, filed on Jun. 29, 2000.
(60) Provisional application No. 60/144,578, filed on Jul. 19, 1999.

(51) Int. Cl.[7] .......................... G01N 31/10; G01N 1/12

(52) U.S. Cl. ................... 436/37; 73/863.41; 73/863.51; 73/863.52; 73/863.53; 73/863.57; 73/863.81; 73/863.85; 436/178; 436/183; 422/62; 422/69; 422/88

(58) Field of Search .............................. 73/863, 863.41, 73/863.51, 863.52, 863.53, 863.57, 863.58, 863.81, 863.85, 863.86; 436/37, 178, 183, 62, 69, 88; 422/69, 88

(56) References Cited

U.S. PATENT DOCUMENTS

| 3,787,183 | A | * | 1/1974 | Kennedy, Jr. ................ 436/37 |
| 4,046,014 | A |   | 9/1977 | Boehringer et al. |
| 4,294,124 | A |   | 10/1981 | Kalwaitis |
| 4,537,071 | A |   | 8/1985 | Waterman |
| 4,837,374 | A |   | 6/1989 | Brown et al. |
| 4,916,956 | A |   | 4/1990 | Semerak et al. |
| 4,980,294 | A |   | 12/1990 | Elias et al. |
| 5,545,377 | A | * | 8/1996 | Fukaya et al. ............. 422/108 |

* cited by examiner

Primary Examiner—Arlen Soderquist
(74) Attorney, Agent, or Firm—Mayer Brown Rowe & Maw LLP

(57) ABSTRACT

An instrument comprising a housing (30) having a fluid-tight seal and a probe (10), adapted to carry a catalyst or sorbent (37), for monitoring a process fluid stream or the behavior of a catalyst or sorbent placed therein. The use of such an instrument permits investigation of catalyst or sorbent behavior in process fluid streams without the need for process shut down or construction of separate process equipment.

19 Claims, 4 Drawing Sheets

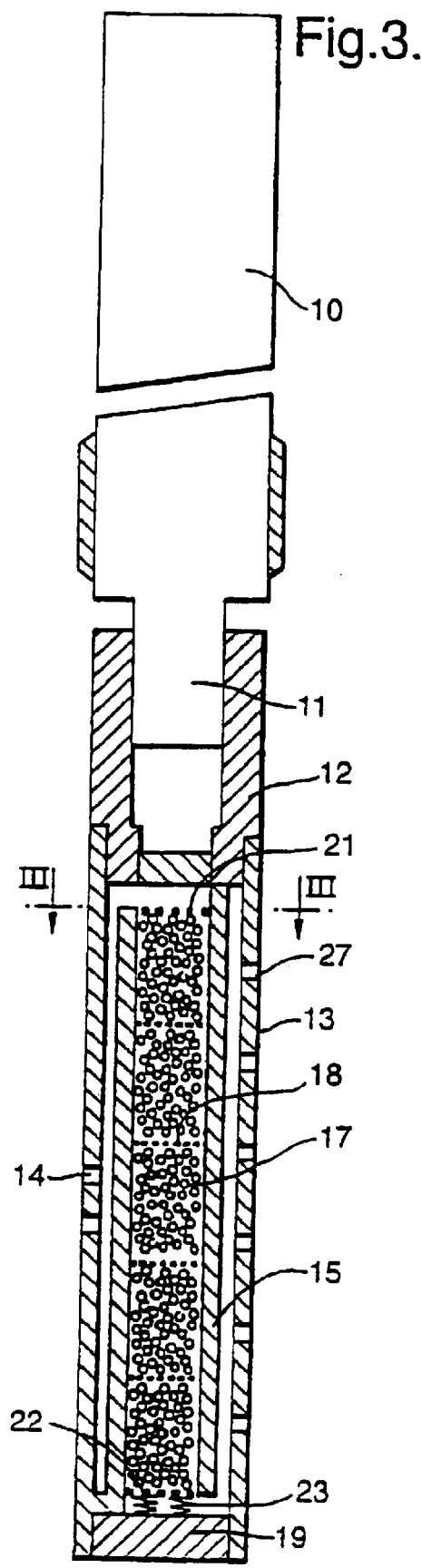
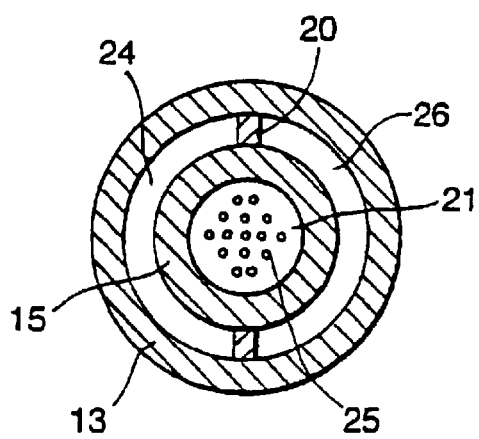
Fig.3.
Fig.4.

MONITORING INSTRUMENT

This is a Continuation of International Application No. PCT/GB00/02519 filed Jun. 29, 2000 which designated the U.S. and was published in the English language, and which claims the benefit of U.S. Provisional Application No. 60/144,578 filed Jul. 18, 1999. Both the PCT application and the provisional application are hereby incorporated in their entirety by reference.

The present invention relates to apparatus for monitoring process streams or the behaviour of catalysts and sorbents, and to methods for use of such apparatus.

Monitoring process streams or the behaviour of catalysts and sorbents in process fluid streams is of considerable importance to the oil and gas, chemicals and catalysts industries. The term "fluid" is used herein to describe a gas or liquid stream or mixtures of these. Typically catalysts and sorbents are affected by trace impurities such as sulphur, arsenic or mercury in process streams and monitoring the levels of these contaminants and/or their affect on catalysts is of vital importance. Current techniques for examining processes or catalysts and sorbents rely upon either insertion of the catalyst or sorbent into reactor vessels in a basket or other container, or the construction of a side-arm loop in a pipeline in which a small reactor or vessel, containing the catalyst or sorbent, is placed. These techniques necessitate process shut-down for the safe insertion of the catalyst or sorbent resulting in considerable costs and lost production.

It is known to monitor corrosion by inserting a probe carrying a coupon of the material under test into a fluid stream. Such probes are typically placed in pipelines by means of an existing valve assembly through which they are inserted. A fluid-tight seal is provided by means of a housing that can be attached to a suitable port, e.g. a valve assembly. The housing partially encloses the length of the probe and contains a suitable packing seal. For monitoring on-line processes generally the housing is connected to the closed valve assembly whilst the process is in-line. At this point the probe is fitted in a retracted position within the housing. When the valve is opened the probe is advanced into the process stream. The packing seal around the shaft of the probe maintains the pressure integrity of the process equipment.

In the present invention, the term "probe" means a device, typically of rod shape, suitable for insertion via a fluid-tight seal into a process fluid stream.

Accordingly, the present invention provides an instrument comprising a housing having a fluid-tight seal and a probe, adapted to carry a catalyst or sorbent. We also provide a method for monitoring a process fluid stream using such a monitoring instrument. The use of such an instrument permits investigation of catalyst or sorbent behaviour in process fluid streams without the need for process shut down or construction of separate process equipment.

It is an object of the invention to use such instruments for conditioning of catalysts or sorbents or the investigation of process fluid streams in regard to contaminant impurities such as water, hydrogen chloride, sulphur and sulphur compounds, arsenic and mercury and their effect upon catalysts and sorbents.

In a second aspect, the present invention provides a method for monitoring a process fluid stream using a monitoring instrument as described above which comprises steps of; (i) inserting the probe carrying the catalyst or sorbent in the process fluid stream whereby the process fluid stream contacts said catalyst or sorbent for a period of time; (ii) passing the process fluid stream over and/or through the said catalyst or sorbent; and thereafter (iii) removing the probe from the process fluid stream.

By the term "sorbent" we necessarily include both absorbent and adsorbent.

The probe comprises a shaft on which the catalyst or sorbent is supported or contained, such that the process fluid is able to flow over or through the catalyst or sorbent. The catalyst or sorbent may be supported directly on the shaft of the probe. This may be achieved by fixing shaped units of the catalyst or sorbent to the shaft or by coating the shaft with the catalyst or sorbent by any means known to those skilled in the art.

In a preferred embodiment, the catalyst or sorbent is particulate and contained within a perforated container. This container may be permanently fixed to the shaft or it may be attached via a connector such as a threaded or flanged connector. The perforated container may be cylindrical, conical, an open basket or any other shape suitable for containment of catalyst or sorbent. In a preferred embodiment, the perforated container is cylindrical.

To minimise the risk of degradation of catalyst or sorbent particles by high velocity process fluid streams, it is preferred to contain the catalyst or sorbent within a container positioned within a second outer container so that the latter shields the catalyst or sorbent particles.

The disposition of inner and outer containers, the use of baffles connecting them and the number and size of the orifices, i.e. perforations, may be so designed as to permit the flow of process fluid across the catalyst or sorbent in-line with the process fluid stream or transverse to the process fluid stream. Such versatility enables a wider range of use in monitoring the process streams and catalyst or sorbent behaviour.

Accordingly, in a first preferred embodiment, the present invention provides a probe comprising a shaft on which are fitted two concentric, hollow cylinders joined by baffles, wherein the catalyst or sorbent is contained in the inner cylinder, both cylinders having a plurality of orifices. The ends of the cylinders are closed and the position and size of the orifices and baffles are such that the process fluid may pass through the catalyst or sorbent chordally at a rate suitable for monitoring impurities in the process fluid stream, or the behaviour of catalyst or sorbent contained therein.

In a second embodiment of the present invention the inner cylinder is non-perforate but open-ended and is disposed within the outer cylinder such that the process fluid is able to pass through the ends of the inner cylinder and thereby axially through the catalyst or sorbent contained therein. The catalyst or sorbent in such a design may be supported at the ends of the inner cylinder by means of perforated members. The perforated member may be a wire mesh or plate containing orifices. If a plate containing orifices is used, the size and number of orifices may be designed to moderate the flow of process fluid through the catalyst or sorbent. When the process fluid has passed through the catalyst or sorbent, it may pass out of the outer cylinder by means of orifices placed therein.

In a third embodiment of the present invention the control of process fluid into the inner cylinder is made by an arrangement of baffles connecting the outer and inner cylinders whereby the process fluid stream is forced, once it has passed through orifices in the outer cylinder, to follow a serpentine path through the annulus between the cylinders before entering the catalyst or sorbent. By the term "serpentine" we mean a path where the process fluid is forced to return in an alternating manner across the surface of the inner cylinder. The baffles may be fixed in any manner that controls the flow of process fluid into the catalyst or sorbent. Preferably they arranged within the annular space between the outer and inner cylinders, in a parallel manner and perpendicular to the axis of the cylinders. Further baffles parallel to the axis of the cylinders, prevent the flow of process fluid around the entire circumference of the inner cylinder and thereby force the process fluid to travel through the serpentine path through annulus and enter the catalyst or sorbent. The inner cylinder again is open-ended and process fluid is able to pass axially through the catalyst or sorbent contained therein. The catalyst or sorbent in such a design may again be supported at the ends of the inner cylinder by means of perforated members. When the process fluid has exited the catalyst or sorbent it may pass out of the outer cylinder by means of orifices placed therein.

Accordingly, if the concentration of a component of the process fluid stream that reacts in the presence of the catalyst or is sorbed by the sorbent under test is known, with the aforementioned arrangements providing for controlled flow rates through the catalyst or sorbent, it may be possible to perform a mass balance calculation. This data can be used to infer how a large-scale reactor of the catalyst or sorbent being tested would perform in terms of removing the said impurity.

The position, size and number of orifices will vary depending upon the design of the probe and the particle size of the catalyst or sorbent to be used. In a design having inner and outer cylinders whereby the process fluid is to flow chordally across the catalyst or sorbent, the orifices preferably number between 1 and 25, and more preferably between 5 and 20, on either side of the outer cylinder and between 1 and 50, and more preferably between 5 and 30 on either side of the inner cylinder. The orifices may be placed in any arrangement that allows the process fluid stream to readily flow through the wall of the cylinder but are preferably arranged in a linear fashion down the length of the cylinders' walls.

In a design having inner and outer cylinders whereby the process fluid is to flow axially through the catalyst or sorbent, the orifices will preferably number between 1 and 20, and more preferably between 1 and 10, on either side of the outer cylinder. The inner cylinder preferably will not contain orifices on its sides. The orifices in this case may be placed in support plates at either end of the inner cylinder. The number of orifices in the support plates will vary depending upon the design of the probe. Preferably the orifices in each of the support plates will number between 1 and 20 orifices and more preferably between 1 and 15.

The size of the orifices will vary depending on the design of the probe and the particle size of the catalyst or sorbent to be used. Preferably the orifices in the outer cylinder, inner cylinder and/or support plates will range from 0.1 mm to 5 mm in diameter.

In an embodiment where the process fluid is forced to travel in a serpentine path between the outer and inner cylinders, the number of baffles perpendicular to the axis of the cylinders may be between 1 and 50 and preferably between 5 and 30.

In any embodiment, wire mesh dividers may also be placed within the inner cylinder to segregate catalyst or sorbent particles into a series of "beds" to allow a more detailed analysis of the sample to be performed upon discharge from the probe. The number of mesh dividers will vary depending upon the design of the probe. Preferably up to 5 mesh dividers may be used.

The catalyst or sorbent may be placed within the cylinders through either end and secured by means of screw cap. This may either be placed at the end fitted to the shaft or to the end placed in the process fluid stream. In a preferred embodiment, the screw cap is fitted to the end placed in the process fluid stream and on closing compresses one or more compression springs against a support plate holding the catalyst or sorbent within the inner cylinder. The compression spring or springs force the plate against the catalyst or sorbent such that on shrinkage or movement of the catalyst or sorbent, the catalyst or sorbent particles remain in mutual contact.

The cylinder may be attached to the shaft by means of a screw thread or other suitable fixing technique such that should it be desired, replacement cylinders may be readily fitted.

The disposition of the probe within the process fluid stream may be by means of a valve assembly, pipeline branch, manhole port with valve stub or any other suitable point of entry. If desired, alignment of the orifices on the outer cylinder wall of the probe with the process fluid stream may be made by means of an identifying mark or arrow on the shaft of the probe. The position of the orifices on the outer cylinder should also be such that they fall within the part of the process fluid stream desirable for monitoring.

The shaft and cylinder containing catalyst or sorbent should be of a size suitable for insertion into pipelines or reaction vessels through valve assemblies or other such entry points as appropriate. The probe size (length and diameter) will depend, for example, upon the internal diameter of the pipeline and means by which the probe is placed in the process fluid stream. The wall thickness of the cylinders should be appropriate for use in the process fluid stream. For example a probe of diameter 16 mm (outside diameter), having a cylinder assembly of 90 mm length and wall thickness 1 mm is suitable for use with pipelines of up to 100 mm (inside diameter) and may be passed for example, through a stub valve with a 19 mm nominal bore.

Valve types suitable for use with probes of the invention are those having a straight path through the valve when in an open position. Such valves include ball valves and gate valves. In one embodiment of the present invention the probe is designed to fit though a ball valve fitted to a pipeline branch. The ball valve is turned using a valve actuator into the open position and the solid shaft passed through it such that the cylinder containing the catalyst or sorbent effectively samples the process stream into which it is being placed.

Leakage of gas or liquid is prevented by means of a suitable seals fitted to a housing. The seals should be any type that prevents any leakage of gas or liquid. For example, PTFE or GRAPHOYL packing rings can be used. In the present invention, the term "housing" means a device for ensuring a fluid-tight seal may be achieved when the probe is inserted into a process stream. The housing may be fitted by any suitable means to the valve assembly prior to insertion of the probe. The materials of construction of the probe should be any compatible with the duty, for example stainless steel or carbon steel.

The monitoring instrument of the invention may be used in a variety of application areas. For example, in a continuous process that involves the passing of a process fluid stream over or through a catalyst bed, a probe may be used carrying a sample of the same catalyst and placed in the process fluid stream upstream of the catalyst bed. In this way, potential catalyst contaminants present in the process fluid stream can be identified. Placing the probe carrying the catalyst at various differing positions within the process equipment allows for understanding how the catalyst behaves under different operating conditions. In addition, positioning of a probe carrying a sample of catalyst or sorbent downstream of a catalyst or sorbent bed within a process fluid stream can allow for monitoring of when the beds become saturated.

For the method for monitoring the process fluid stream, the process fluid stream may be either in the liquid or gaseous phase, or it may be a mixed phase. In a mixed phase process fluid stream, positioning of a probe carrying a sample of the catalyst or sorbent at various positions can help to understand the effects of the mixed phase on the process itself. Process fluid streams that may be monitored using an instrument of this invention include hydrocarbon gas streams, natural gas, air, synthesis gas streams (mixtures of CO, $CO_2$, $H_2$ and $CH_4$) or hydrogen. Gas velocities to which the probe may be exposed range from 10 to 30 meters per second.

Operating temperatures and pressures will vary depending upon the process stream in which the probe is to be placed and the seal system used. Operating temperatures ranging from −30° C. to 450° C. are possible with the probe of the invention. If PTFE packing rings are used, the temperature range is preferably −30° C. to 260° C. If GRAPHOYL packing rings are used, the temperature range is preferably −30° C. to 450° C. Operating pressures dictate which type of seal system is used. For example, the operating pressure may range from 0.5 bar abs. to 100 bar abs. with PTFE packing rings or 0.5 bar abs. to 68 bar abs. with GRAPHOYL packing rings.

The catalysts or sorbents that may be suitable for the monitoring of process fluid streams described above include metal oxides or mixtures of metal oxides or hydroxides such as zinc oxide, iron oxide, copper oxide or chromium oxide; sulphides such as copper sulphide; carbonates such as copper carbonate; and supported metals such as copper, cobalt, nickel, molybdenum, platinum or ruthenium on oxide supports such as alumina, silica, aluminosilicates, titania, zirconia, activated carbon and zeolites. The quantities of catalyst or sorbent used within the cylinder will vary depending upon the design of the probe. Volumes may range from 0.5 $cm^3$ to 100 $cm^3$ and preferably from 1 $cm^3$ to 30 $cm^3$. The catalyst or sorbent particle size will vary depending upon the type used and the design of the probe. Particles may take the form of pellets, extrusions or granules. Preferably the particles will be sized appropriately for the dimensions of the containing space, e.g. the cylinder in which they are positioned to ensure that the catalyst or sorbent has suitable contact with the process stream. Preferably the catalyst and sorbent particle sizes will vary from 0.5 mm to 15 mm and have an aspect ratio of between 1 and 3.

Probes of the invention are particularly useful for examining process fluid streams without the need for process shutdown. This may be achieved by connection of the probe to an existing valve branch on a pipeline, or manhole port with valve stub, or any other suitable point of entry. In a preferred embodiment of the invention, the probe and housing are first attached by any suitable means to a pipeline branch valve assembly. The valve between the pipe and the probe is then opened. When the pressure in the pipeline and housing have equalised, the probe is then inserted through seals in the housing to position the cylinder containing the catalyst or sorbent within the process fluid stream. Direction arrows may then be used to orient the cylinders with respect to the fluid flow. Monitoring times can vary from a few hours to several months. Shorter times may be more appropriate for testing physical adsorbency characteristics or fouling of sorbents or catalysts. Medium or longer times may be more appropriate for looking at irreversible chemical reaction with absorbents or poisoning or sintering. Once an appropriate period has passed, to remove the cylinder for analysis, the probe is first withdrawn past the valve, the valve closed, and the pressure in the probe housing released. The probe may then be fully removed and the cylinder detached. The catalyst or sorbent may then be recovered for analysis. Many analytical techniques can be applied to the removed sample such as chemical analysis, including specific tests for certain absorbed compounds or catalyst poisons such as sulphur. Physical changes may be measured using porosimetry, microscopy and other tests to establish any change in micromimetrics, surface area and surface topography.

The invention will now be described with reference to the accompanying drawings in which:

FIG. 3 is a diagrammatic cross section of a probe in accordance with a second embodiment.

FIG. 4 is a cross section of the probe depicted in FIG. 3 along the line of III-III.

Figure 1:
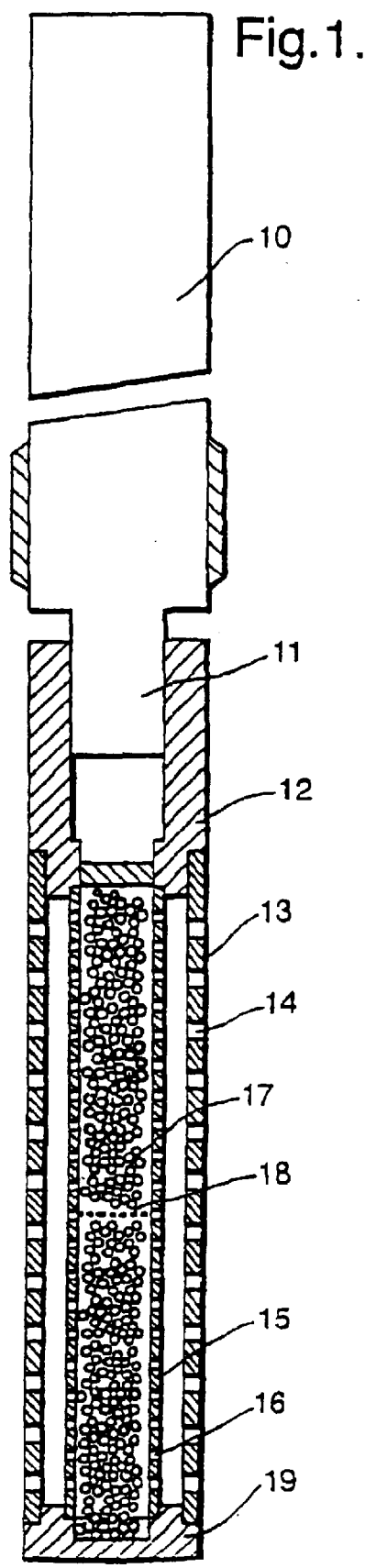
FIG. 1 is a diagrammatic cross section of a probe in accordance with a first embodiment.
Figure 2:
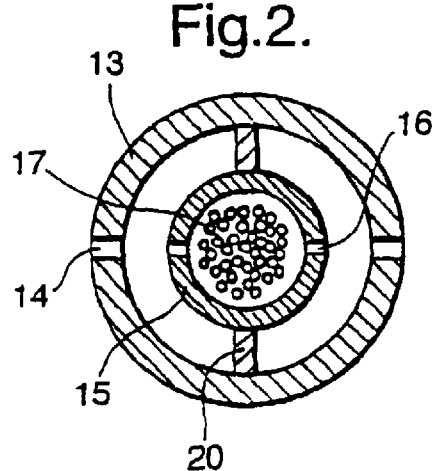
FIG. 2 is a cross section of the probe depicted in FIG. 1

Referring to the drawings, FIGS. 1 and 2 shows a solid shaft (10) connecting through a screw threaded bolt (11) to a cylinder support (12) carrying a hollow outer cylinder (13) of length 90 mm and internal diameter 14 mm. This cylinder has 12×3.5 mm orifices (14) evenly spaced on each side to allow gas or liquid to enter the cylinder. Within the outer cylinder is an inner hollow cylinder (15) of length 90 mm and internal diameter 10 mm, again containing a plurality of orifices (16), numbering 20×1.5 mm on each side. Within the inner cylinder is 6 $cm^3$ of particulate catalyst or sorbent material (17). This material may be segregated using a wire mesh (18). At the base of the cylinder is the end cap (19). The inner cylinder (15) is fixed to the outer by means of baffles (20) running the length of the cylinder and having a cross section of 2 mm×1 mm. These baffles prevent the flow of process fluid around the circumference of the inner cylinder and force it to pass through the catalyst or sorbent contained within the inner cylinder. The position of orifices in the inner and outer cylinders allows the process fluid to pass chordally through the catalyst or sorbent.

In a second embodiment of the invention shown in FIGS. 3 and 4, the number of upstream orifices (14) are fewer than the number of downstream orifices (27) and are sized to enable the process fluid to enter the cylinder at a calculable rate. The inner cylinder (15) is open ended, has no orifices in its walls, and is fixed so that the process fluid is forced to enter the cylinder through a fixed upper support plate (21) containing orifices. The process fluid passes through the length of the catalyst or sorbent (17) that may be separated by mesh dividers (18). The process fluid exits the catalyst or sorbent through a lower support plate containing orifices (22). This plate is held in place by compression springs (23) that are compressed by the screw-threaded end-cap (19). The outer cylinder (13) is connected to the inner cylinder (15) by means of longitudinal baffles (20) that prevent the process fluid, entering through upstream orifices from moving around the full circumference of the inner cylinder. The process fluid is forced upwards though the annular space (24) and then downward through the upper support plate (21) containing orifices (25). After exiting the base of the inner cylinder the process fluid is now able to travel up the annular space (26) and exits the outer cylinder through the orifices (27) on the downstream side.

Figure 5:
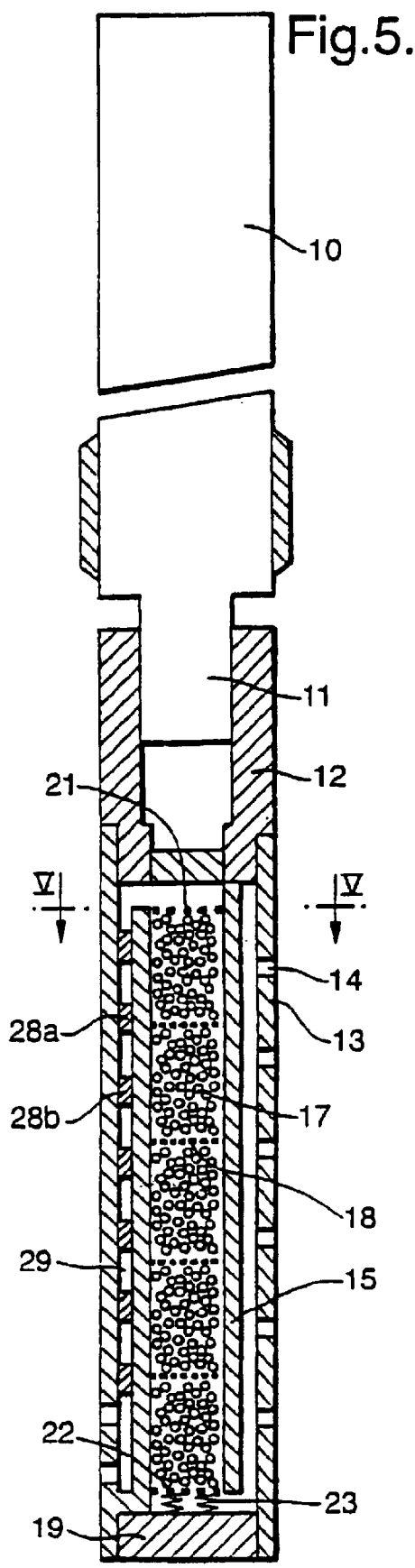
FIG. 5 is a diagrammatic cross section of a probe in accordance with a third embodiment.
Figure 6:
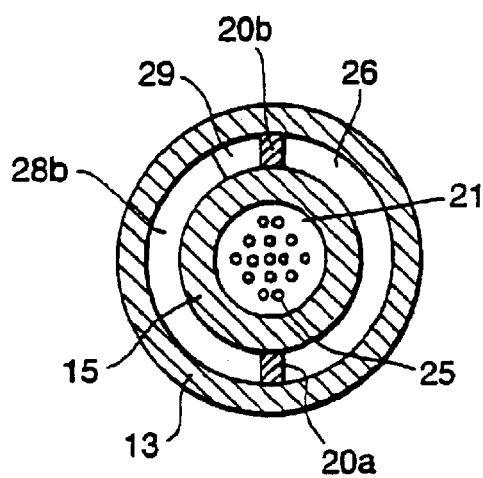
FIG. 6 is a cross section of the probe depicted in FIG. 5 along the line of V-V.

In a third embodiment of the invention shown in FIGS. 5 and 6, baffles (28a, 28b) are present between the outer and inner cylinders that force the process fluid to follow a serpentine path through the annulus (29) between the cylinders. The process fluid enters through orifices (14) on the upstream side of the outer cylinder (13). This is connected to the inner cylinder (15) by means of part-circumferential baffles (28a, 28b) and longitudinal baffles (20a, 20b). Alternate baffles (28a) shop short of baffle (20a) and baffles (28b) stop short of baffle (20b) creating the annular path (29). The combined effect of these baffles is to force the process fluid to take a controlled serpentine path through the annulus. The process fluid is forced upwards though the alternating annular space (29) and then downward through the upper support plate (21) containing orifices (25). After exiting the base of the inner cylinder the process fluid is now able to travel up the annular space (26) and exits the outer cylinder through the orifices (27) on the downstream side.

The position and number of orifices in the cylinders and the disposition of the internal baffles thus enables the process fluid to pass in an axial manner through the catalyst or sorbent in a controlled manner. Such control enables a mass-balance calculation to be performed and thereby the exposure of the catalyst or sorbent to the process stream contaminant to be determined. Subsequent analysis of the catalyst or sorbent can therefore be related directly to the quantity of process fluid to which they have been exposed, yielding valuable data on process stream contaminants and catalyst or sorbent behaviour.

Figure 7:
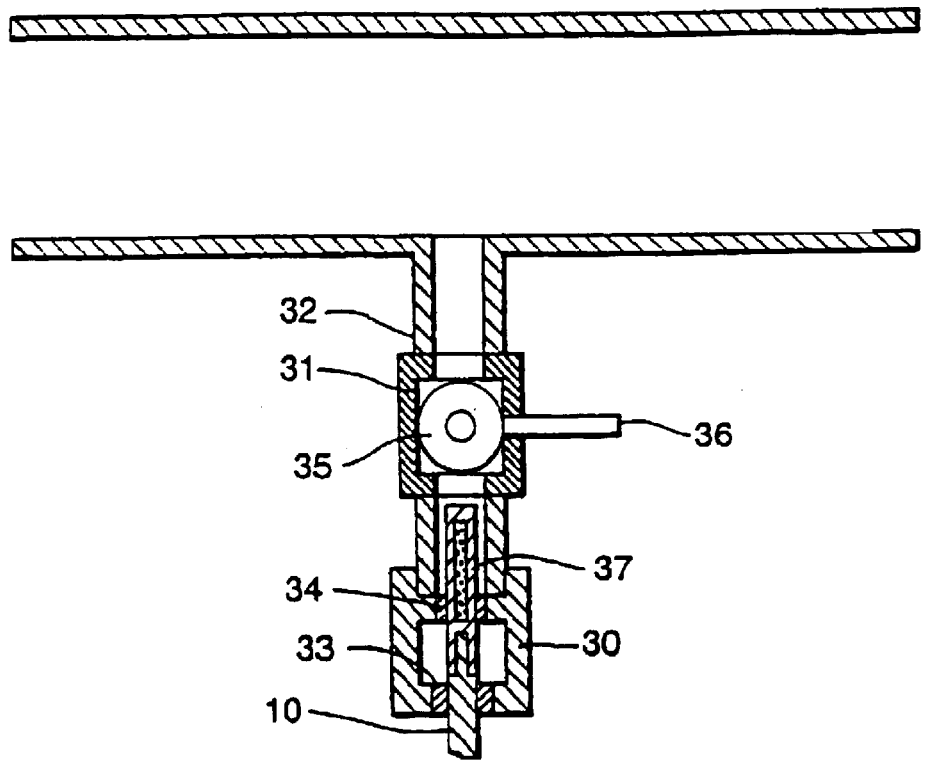
FIG. 7 is a section of a pipeline having a valve assembly for the insertion of a probe.
Figure 8:
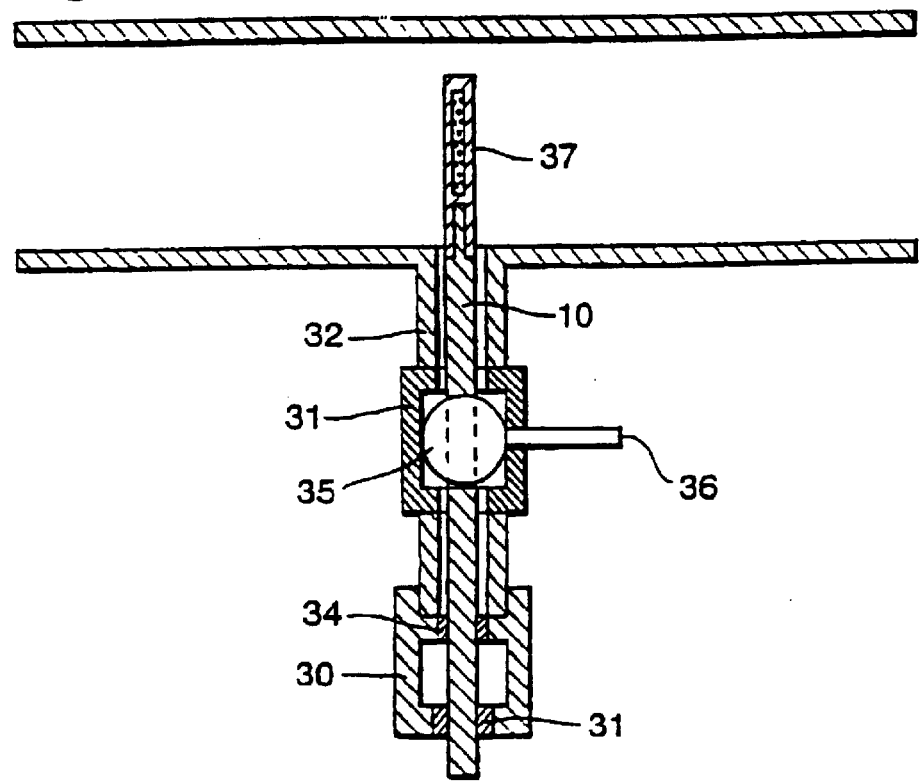
FIG. 8 is a view similar to FIG. 7 with the probe in the operating position.

Referring to FIGS. 7 and 8, which illustrate a shaft (10) and housing (30) fixed to a valve assembly (31) on a pipeline branch (32). The housing is first fitted to the pipeline branch and then the probe inserted through outer and inner seals (33) and (34). The ball valve (35) is in a closed position. The valve actuator (36) may then be turned and the valve opened. The probe may then be fully inserted (see FIG. 8) and the cylinder containing catalyst or sorbent (37) positioned within the process stream. Probe removal is achieved by withdrawing the probe beyond the ball valve, dosing the valve, then releasing any pressure in the probe housing and removing the probe. The housing may then be detached.

Thus the present invention permits investigation of catalyst or sorbent behaviour in process fluid streams without the need for process shut down or construction of separate process equipment.

What is claimed is:

1. An instrument comprising
   (i) a housing for attachment to a vessel or pipeline through which a process fluid is flowing and
   (ii) a probe having
      (a) a shaft which may be inserted into or withdrawn from said vessel or pipeline through sealing means associated with said housing, and
      (b) a container for containing a catalyst or sorbent, said container being fixed to one end of said shaft
   whereby, by insertion of said shaft into said vessel or pipeline, said container is retractably disposed within said vessel or pipeline; said container comprising an outer container, having walls with orifices therein, and an inner container for containing the catalyst or sorbent, said inner container being disposed within said outer container such that the inner container and outer container are spaced apart from each other to form an unstream and a downstream region between the inner container and the outer container, said upstream and downstream regions being separated from one another by baffle means, whereby, when inserted into a vessel or pipeline through which a process fluid is flowing, at least a part of the process fluid can flow from upstream of said outer container through at least one orifice in the wall of the outer container into said upstream region, through said catalyst or sorbent contained within the inner container, into said downstream region, and thence through at least one orifice in the wall of the outer container to the vessel or pipeline downstream of the container.

2. An instrument according to claim 1, wherein said inner container fixed is within said outer container, said inner container having at least one orifice in the upstream region and at least one orifice in the downstream region and baffles between the outer container and said inner container dividing said upstream region from said downstream region such that process fluid flows in a substantially axial or transverse manner through said catalyst or sorbent.

3. An instrument according to claim 2, wherein mesh dividers are present to separate catalyst or sorbent into separate beds within the inner container.

4. An instrument according to claim 1, wherein said inner container is a non-perforate cylinder which is open ended and disposed within the outer container such that the process fluid is able to pass through the ends of the inner container and thereby axially through a bed of catalyst or sorbent contained therein.

5. An instrument according to claim 4, wherein a perforated member is provided at each end of the inner container for supporting the catalyst or sorbent contained therein.

6. An instrument according to claim 1, wherein the inner container is bounded by a wall or walls provided with orifices.

7. An instrument according to claim 6, wherein the inner container has from 1 to 50 orifices in its walls.

8. An instrument according to claim 1, wherein the arrangement of baffles connecting the outer container and the inner container is adapted to direct the process fluid stream to follow a serpentine path through the annulus between the cylinders before entering the catalyst or sorbent.

9. An instrument according to claim 8, wherein said inner container is a non-perforate cylinder which is open ended and disposed within the outer container such that the process fluid is able to pass through the ends of the inner container and thereby axially through a bed of catalyst or sorbent contained therein.

10. An instrument according to claim 9, wherein a perforated member is provided at each end of the inner container for supporting the catalyst or sorbent contained therein.

11. An instrument according to claim 1, wherein the outer container has from 1 to 25 orifices in its walls.

12. A method for monitoring a process fluid stream or the behaviour of a catalyst or sorbent in said stream using an instrument comprising;
   (i) a housing for attachment to a vessel or pipeline through which a process fluid is flowing and
   (ii) a probe having
      (a) a shaft which may be inserted into or withdrawn from said vessel or pipeline through sealing means associated with said housing, and
      (b) a container for containing a catalyst or sorbent, said container being fixed to one end of said shaft
   whereby, by insertion of said shaft into said vessel or pipeline, said container is retractably disposed within said vessel or pipeline;

said container comprising an outer container, having walls with orifices therein, and an inner container for containing the catalyst or sorbent, said inner container being disposed within said outer container such that the inner container and outer container are spaced apart from each other to form an upstream and a downstream region between the inner container and the outer container, said upstream and downstream reasons being separated from one another by baffle means, whereby, when inserted into a vessel or pipeline through which a process fluid is flowing, at least a part of the process fluid can flow from upstream of said outer container through at least one orifice in the wall of the outer container into said upstream region, through said catalyst or sorbent contained within the inner container, into said downstream region, and thence through at least one orifice in the wall of the outer container to the vessel or pipeline downstream of the container comprising the steps of:
(i) attaching said housing to a valve assembly fixed to a pipeline or vessel through which said process fluid stream is flowing,
(ii) opening said valve,
(iii) passing the probe containing a catalyst or sorbent through said sealing means in said housing and thence through the opened valve into the process fluid stream whereby part of the process fluid stream passes through said catalyst or sorbent for a period of time; and thereafter
(iv) removing the probe from the process fluid stream.

13. A method according to claim 12, wherein the process fluid stream is flowing transverse to the probe at rate equivalent to gas velocities between 10 and 30 metres per second.

14. A method according to claim 12, wherein said inner container is fixed within said outer container, said inner container having at least one orifice in the upstream region and at least one orifice in the downstream region and baffles between the outer container and said inner container dividing said upstream region from said downstream region and direct the flow of the process fluid in a substantially axial or transverse manner through said catalyst or sorbent.

15. A method according to claim 14, wherein mesh dividers are present to separate catalyst or sorbent into separate beds within the inner container.

16. A process according to claim 12, wherein the catalysts or sorbent contained in the inner container is selected from the group consisting of metal oxides or mixtures of metal oxides or hydroxides, sulphides, carbonates and metals supported on an oxide support.

17. A process according to claim 16, wherein the catalysts or sorbent contained in the inner container is selected from the group consisting of zinc oxide, iron oxide, copper oxide, chromium oxide, copper sulphide, copper carbonate, and a metal selected from copper, cobalt, nickel, molybdenum, platinum or ruthenium said metal being supported alumina, silica, an aluminosilicate, titania, zirconia, activated carbon or a zeolite.

18. A process according to claim 12, wherein the volume of the catalyst or sorbent contained within the inner container is from 0.5 to 100 $cm^3$.

19. A process according to claim 12, wherein the catalyst or sorbent contained within the inner container is in the form of particles having a size between 0.5 mm and 15 mm.

* * * * *

UNITED STATES PATENT AND TRADEMARK OFFICE
CERTIFICATE OF CORRECTION

PATENT NO. : 6,869,800 B2
DATED : March 22, 2005
INVENTOR(S) : Robert D. Torgerson et al.

It is certified that error appears in the above-identified patent and that said Letters Patent is hereby corrected as shown below:

Column 8,
Line 2, "unstream" should read -- upstream --.

Signed and Sealed this

Twenty-second Day of November, 2005

JON W. DUDAS
*Director of the United States Patent and Trademark Office*